US 6,751,560 B1

(12) United States Patent
Tingley et al.

(10) Patent No.: US 6,751,560 B1
(45) Date of Patent: Jun. 15, 2004

(54) NON-INVASIVE PIPELINE INSPECTION SYSTEM (75) Inventors: Robert Tingley, Ashland, MA (US); Claude P. Brancart, Brunswick, ME (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 91 days.

(21) Appl. No.: 09/655,954

(22) Filed: Sep. 6, 2000

Related U.S. Application Data (60) Provisional application No. 60/222,170, filed on Aug. 1, 2000.

(51) Int. Cl.[7] .............................................. F17D 5/06
(52) U.S. Cl. ....................................................... 702/51
(58) Field of Search .............................. 702/51; 73/629, 73/632, 620, 638, 643; 324/639, 633, 635; 359/125; 367/35; 219/687, 679; 204/157

(56) References Cited

U.S. PATENT DOCUMENTS

| | | | | |
|---|---|---|---|---|
| 3,634,753 A | * | 1/1972 | Unterberger | 324/6 |
| 3,950,695 A | | 4/1976 | Barringer | 324/3 |
| 3,974,680 A | | 8/1976 | Beaver | 73/40.5 |
| 3,978,396 A | | 8/1976 | Inouye et al. | 324/6 |
| 4,092,868 A | * | 6/1978 | Thompson et al. | 73/638 |
| 4,161,687 A | | 7/1979 | Lytle et al. | 324/6 |
| 4,603,584 A | | 8/1986 | Bartle et al. | 73/599 |
| 5,155,439 A | | 10/1992 | Holmbo et al. | 324/534 |
| 5,303,079 A | * | 4/1994 | Gnauck et al. | 359/188 |
| 5,392,652 A | * | 2/1995 | Levesque et al. | 73/629 |
| 5,455,516 A | * | 10/1995 | Jean et al. | 324/639 |
| 5,500,730 A | | 3/1996 | Johnson | 356/73.1 |
| 5,612,625 A | | 3/1997 | Suyama et al. | 324/635 |
| 5,719,503 A | | 2/1998 | Burnett | 324/534 |
| 5,864,232 A | | 1/1999 | Laursen | 324/220 |
| 5,987,990 A | | 11/1999 | Worthington et al. | 73/592 |
| 5,990,689 A | | 11/1999 | Poncon | 324/627 |
| 5,995,447 A | * | 11/1999 | Mandal et al. | 367/35 |
| 6,307,191 B1 | * | 10/2001 | Waycuilis | 219/687 |

FOREIGN PATENT DOCUMENTS

| | | | | |
|---|---|---|---|---|
| JP | 181146 A | | 7/1995 | G01N/22/00 |
| JP | 123108 A | | 5/1998 | G01N/29/20 |
| JP | 411270800 A | * | 10/1999 | F17D/5/06 |
| WO | 46545 A | | 8/2000 | F17D/3/01 |

OTHER PUBLICATIONS

Cheo et al., "Detection Of Voids And Contaminants In Polyethylene Insulated Cable Utilizing A Fir Laser Beam", IEEE Transactions Power Apparatus and Systems, vol. PAS–102, No. 3, Mar. 1983, pp. 521–526.
Gauthier et al., "EMAT Generation Of Horizontally Polarized Guided Shear Waves For Ultrasonic Pipe Inspection", International Pipeline Conference—vol. 1, 1998, pp. 327–334.
Rose et al., "Ultrasonic Guided Wave Inspection Concepts For Steam Generator Tubing", Materials Evaluation, vol. 52, No. 2, Feb. 1994, pp. 307–311.

(List continued on next page.)

Primary Examiner—John Barlow
Assistant Examiner—Tung S Lau
(74) Attorney, Agent, or Firm—Testa, Hurwitz & Thibeault, LLP (57) ABSTRACT

The invention is directed to a system and method for non-invasive pipeline inspection. According to one embodiment, the system includes a processor, an analyzer, and a wave launcher. The wave launcher is adapted to transmit an input wideband waveform having a selected input energy into the pipeline along a longitudinal axis, and to receive from the pipeline a reflected component of the input waveform having a reflected energy. The analyzer is adapted to generate the input waveform, and to receive the reflected component of the input waveform from the wave launcher. The processor is adapted to compare the input waveform with the reflected component of the input waveform to determine characteristics.

56 Claims, 7 Drawing Sheets

OTHER PUBLICATIONS

George A. Alers, "Application Of Special Wave Modes To Industrial Inspection Problems", 1994 International Mechanical Engineering Congress and Exposition—AMD–vol. 188, Nov. 1994, pp. 1–9.

Alleyne et al., "The Effect Of Discontinuities On The Long–Range Propagation Of Lamb Waves In Pipes", Institution of Mechanical Engineers, Part E: Journal of Process Mechanical Engineering, vol. 210, No. E3, 1996, pp. 217–226.

Michael Lowe, "Characteristics Of The Reflection Of Lamb Waves From Defects In Plates And Pipes", Review of Progress In Quantitative Nondestructive Evaluation, vol. 17A, 1998, pp. 113–120.

Cawley et al., "The Use Of Lamb Waves For The Long Range Inspection Of Large Structures", Ultrasonics, vol. 34, No. 2–5, Jun. 1996, pp. 287–290.

Lowe et al., "Defect Detection In Pipes Using Guided Waves", Ultrasonics, vol. 36, No. 1–5, Feb. 1998, pp. 147–154.

PCT International Search Report for International Application No.: PCT/US01/24083, mailed on Jun. 7, 2002.

* cited by examiner

NON-INVASIVE PIPELINE INSPECTION SYSTEM

REFERENCE TO RELATED APPLICATION

This application claims priority to the filing date of U.S. Provisional Patent Application Serial No. 60/222,170 entitled "Non-Invasive Pipeline Inspection Using Radiosounding," filed on Aug. 1, 2000, the disclosure of which is hereby incorporated by reference.

FIELD OF THE INVENTION

This invention relates generally to inspecting a pipeline for anomalies, and more specifically to inspecting a pipeline using a reflected component of an input waveform.

BACKGROUND OF THE INVENTION

To maintain substantial fluid flow through a pipeline, internal pipeline characteristics need to be monitored so that defects, obstructions, and other anomalies in the pipeline can be detected and repaired efficiently. In addition to obstructions affecting fluid flow in the pipeline, a pipeline may bend and/or buckle when it experiences a change in pressure, such as when the pipeline is laid underwater. Frequently, companies must endure substantial monetary costs and schedule delays due to the detection and repair of these pipeline anomalies.

In some conventional systems, an internal, invasive device that crawls the length of the pipeline is used to inspect a pipeline for anomalies. This device, often called a "pig", poses a serious blockage to the normal fluid flow through the pipeline. A pig may additionally require several days for the inspection of a lengthy pipeline. Furthermore, the amount of data a pig can record, the life of its battery, and the wear of its components from crawling the pipeline all limit the usefulness of the pig.

Measuring the acoustic signature of a pipeline is another technique used to detect pipeline anomalies. This technique sometimes involves hitting the pipeline on its side with a hard object, such as a hammer, and then measuring the acoustic signature of the pipeline. Anomalies often alter the acoustic signature of a pipeline as compared to a pipeline with no such anomalies. However, the magnitude of the anomaly that may be detected is dependent upon the wavelength of the waveform transmitted along the pipeline, and sound waves generally have longer wavelengths than some other waveforms. Therefore, this technique typically fails to detect smaller-sized anomalies in a pipeline.

Pulse propagation may also be used to detect pipeline anomalies. According to one technique, two pulses are transmitted along the pipeline from opposing locations towards an intersecting location. The pulses intersect and are each modified by collision with the oppositely directed pulse. A receiver is positioned at the intersecting location and, after receiving the modified pulses, analyzes at least one indicator characteristic of one of the modified pulses to determine whether an anomaly exists between the receiver and the corresponding transmitter. However, this technique usually requires two separate transmitters and a separate receiver, each of which increases the costs associated with detecting anomalies. Also, pulse propagation analysis may further require inserting the receiver into a location in the pipeline not normally open for device placement.

Another conventional approach is an ultrasonic guided wave inspection technique that uses stress waves, such as Lamb waves. Since Lamb waves are typically guided along the pipeline, lateral spreading of the energy associated with these waves does not usually occur and the propagation is essentially one-dimensional. For this reason, Lamb waves normally propagate over longer distances than other types of waves, such as bulk waves. Unfortunately, at least two modes typically exist at any frequency for Lamb waves. Furthermore, the modes are generally dispersive, which means that the shape of the propagating waveform varies with distance along the pipeline. Consequently, interpretation of the signals is difficult and can also lead to signal-to-noise problems.

Accordingly, it is desirable to produce a system that is capable of detecting an internal characteristic of a pipeline in a non-invasive fashion. It is also desirable to be able to inspect a pipeline faster than currently possible, as well as to be able to accurately detect smaller-sized anomalies in a pipeline.

SUMMARY OF THE INVENTION

Briefly, the invention relates to a system and method for inspecting a pipeline. In one embodiment, the invention provides a system for detecting and characterizing an anomaly in a pipeline. In another embodiment, the invention provides a system that can also determine the longitudinal path/shape of the pipeline. With a starting point and the longitudinal shape of the pipeline, a further embodiment of the invention can also determine the location of a pipeline buried underground or even under water. According to one preferred embodiment, the system includes a processor, an analyzer, and a wave launcher. In an alternate embodiment, the analyzer, wave launcher, and processor are incorporated into a single unit, thereby eliminating the external connections between the devices. The wave launcher communicates with the pipeline, and is adapted to transmit an input waveform having a selected input energy along the central longitudinal axis of the pipeline. Examples of the type of input waveform include, but are not limited to, an electromagnetic waveform, a wideband waveform, and an acoustic waveform. Further examples of input wideband waveforms include, but are not limited to, a chirp waveform, a spread spectrum waveform, a wavelet waveform, and a solitons waveform. The wave launcher is further adapted to receive a reflected component of the input waveform having a characteristic reflected energy. An example of the wave launcher includes an antenna adapted to transmit the input waveform along the pipeline.

The analyzer communicates with the wave launcher, and is adapted to generate the input waveform. The analyzer is further adapted to receive the reflected component of the input waveform from the wave launcher. According to a further feature, the analyzer includes a signal generator, energy component devices, and a directional coupler. The signal generator generates the input waveform that is transmitted along the pipeline. The energy component devices extract out the magnitude and phase components of the input energy and the reflected energy associated with the input waveform and the reflected component of the input waveform. An example of the analyzer includes an automated vector network analyzer.

According to one embodiment, the processor communicates with the analyzer, and is adapted to compare the input waveform with the reflected component of the input waveform to generate a mathematical model for the pipeline. According to one feature, the mathematical model includes information regarding the longitudinal path/shape of the pipeline. According to another embodiment, the processor and the analyzer interact to detect and determine the characteristics of an anomaly in the pipeline. Examples of an anomaly in the pipeline include, but are not limited to, an obstruction, a flange, rust, and poorly constructed welds. Specifically, the characteristics of the anomaly include, but are not limited to, the location of the anomaly in the pipeline, the type of anomaly, and the size of the anomaly. According to a further feature, the system of the invention displays the characteristics of the anomaly and/or the shape/location of the pipeline to a user.

In one operational embodiment, the processor initializes the analyzer. Optionally, the processor initializes the analyzer by calibrating it. Illustratively, the processor calibrates the analyzer by temperature stabilizing the analyzer. In one embodiment, once the processor calibrates the analyzer for operation, the user of the inspection system of the invention inputs the diameter of the pipeline into the processor. The processor uses the diameter to determine the frequency range at which the input waveform can propagate along the central longitudinal axis of the pipeline. The processor transmits this frequency range to the analyzer and the analyzer generates the input waveform having a frequency within this range. The analyzer transmits the input waveform to the wave launcher, and the wave launcher launches the input waveform along the central longitudinal axis of the pipeline.

In a further embodiment, the analyzer extracts the input energy associated with the input waveform. When the analyzer receives the reflected component of the input waveform, the analyzer extracts the reflected energy associated with the reflected component. According to another feature, the analyzer then determines a mathematical representation, or transfer function, relating the input energy and reflected energy. The analyzer then transmits this information to the processor.

In one embodiment, the processor determines the energy reflected from the obstruction by generating a mathematical model of the inspection system of the invention and the pipeline. According to this feature, the processor determines a model transfer function relating the input energy of a model input waveform and the model reflected energy associated with a model reflected component. In one embodiment, the processor determines the characteristics of the obstruction from the model transfer function and the transfer function for the input waveform. In some embodiments, the processor determines which mathematical model to use from the transfer function relating the input energy and reflected energy. The processor can use, for example, an ideal physics-based model, an average model, and/or a section-by-section model to model the pipeline.

According to a further feature, the processor displays the characteristics of the anomaly with a textual representation on an output device. Alternatively, the processor displays the characteristics with a graphical user interface, a three-dimensional solids rendering plot, or an echo plot.

In some embodiments of the invention, the pipeline curves along a longitudinal central axis. In one aspect, the user of the inspection system still provides the diameter of the pipeline. Using the diameter, the processor determines a different range of frequencies at which the input waveform can propagate to aid the processor to model the curved pipeline accurately. Once the processor models the curved pipeline accurately, the processor determines the shape of the pipeline, the location of the pipeline, or the characteristics of the obstruction.

BRIEF DESCRIPTION OF THE DRAWINGS

Advantages of the invention will become better understood by referring to the following drawings, which show a system according to an illustrative embodiment of the invention and in which.

DESCRIPTION OF THE ILLUSTRATIVE EMBODIMENTS

Figure 1:
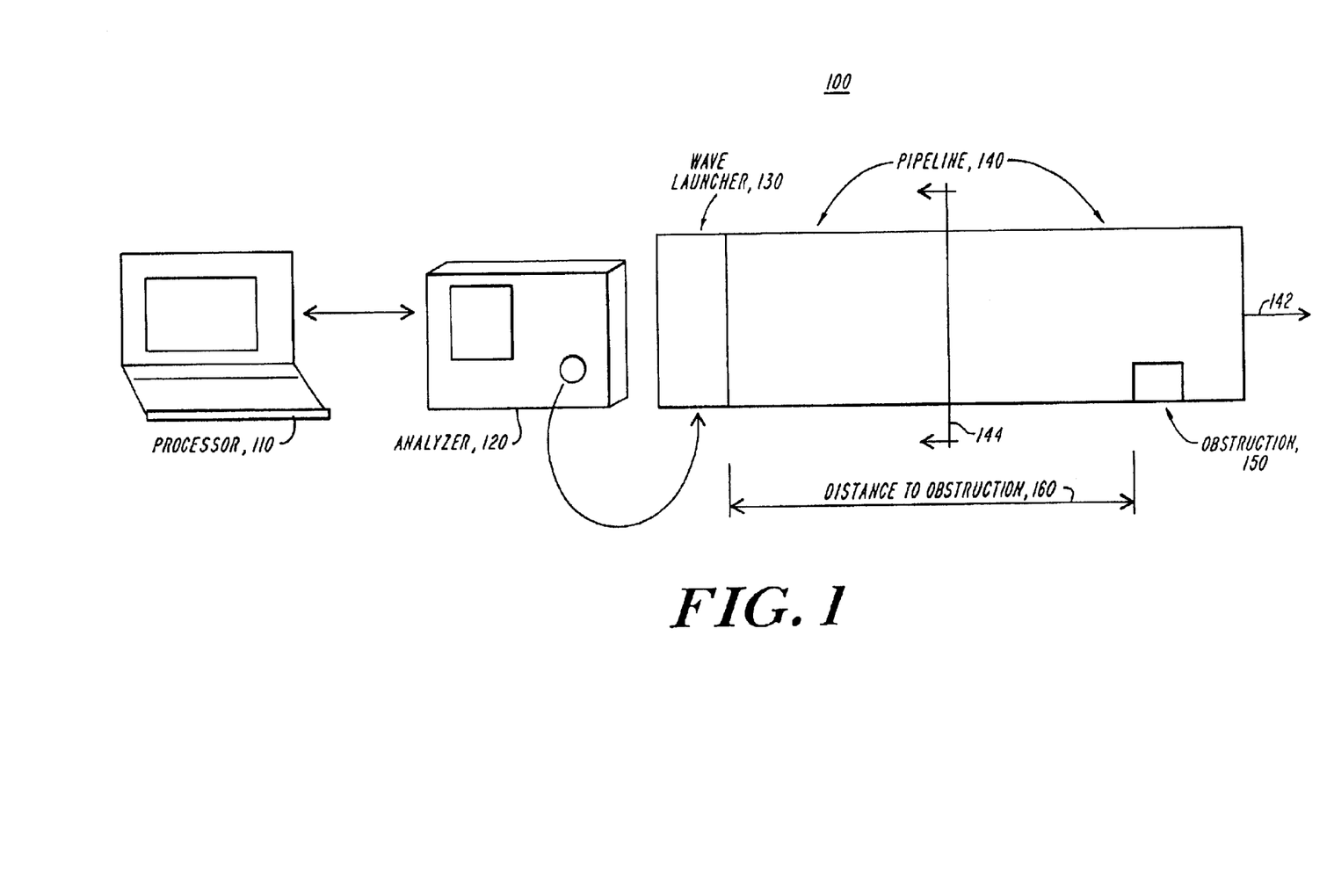
FIG. 1 is a conceptual block diagram depicting the use of a system constructed in accord with an illustrative embodiment of the invention for inspecting a pipeline and/or for determining the curvature of the pipeline along a longitudinal central axis.

FIG. 1 is a conceptual block diagram depicting an illustrative system 100 for inspecting characteristics of a pipeline 140. The illustrative inspection system 100 includes a processor 110, an analyzer 120, and a wave launcher 130. In another embodiment, the processor 110 is incorporated within the analyzer 120, thereby eliminating the external connection between the two devices. In a further embodiment, the processor 110, the analyzer 120, and the wave launcher 130 are incorporated within a single device. As skilled artisans will appreciate, various components of the inspection system 100 can be implemented in hardware, software or both. The pipeline 140 is included in FIG. 1 for clarity, but it is not a component of the illustrative inspection system 100. Preferably, the inner surface of the pipeline 140 is sufficiently conductive to support input waveforms and functions as a waveguide for a suitable axial distance along the pipeline 140. As skilled artisans will appreciate, a sufficiently conductive material may be any of one of a variety of materials, such as, but not limited to, iron, steel, cobalt, nickel, and alloys thereof.

As discussed more fully below, the wave launcher 130 transmits an input waveform along the central longitudinal axis 142 of the pipeline 140. In one embodiment, the wave launcher 130 is an antenna. The analyzer 120, which is in communication with the wave launcher 130, generates an input waveform and transmits it to the wave launcher 130. According to the illustrative embodiment, the input waveform is a wideband waveform, which is a waveform having a bandwidth that forms at least about 0.1% of its center frequency. An example of a wideband waveform is a waveform which distributes its energy uniformly between 250 MHz and 750 MHz, having a ratio of bandwidth to center frequency equal to 1.0 [(750–250)/500=1.0)]. In exemplary embodiments, the system 100 employs input waveforms having a center frequency of about 800 MHz and a bandwidth of about 400 MHz. Examples of potential input waveforms include, but are not limited to, electromagnetic and acoustic waveforms.

The processor 110, which is in communication with the analyzer 120, processes and outputs results of the inspection of the pipeline 140. According to one illustrative embodiment, the characteristic to be detected is the curvature of the pipeline 140 along the longitudinal central axis 142. According to another illustrative embodiment, the characteristic to be detected is the diameter of the pipeline 140. In a further illustrative embodiment, the characteristic to be detected is the shape of a cross-sectional view of the pipeline 140, taken for example along view 144. According to the illustrative embodiment of FIG. 1, the characteristic of the pipeline 140 to be detected is an anomaly in the pipeline 140. In one embodiment, the anomaly is an obstruction 150. In other embodiments, the anomaly may be a flange, rust, partly constructed welds, or the like. In operation the inspection system 100 detects an illustrative obstruction 150 of the pipeline 140 that is located a distance 160 away from the wave launcher 130. In operation, the analyzer 120 selects the amount of input energy to transmit along the pipeline 140.

In an alternate embodiment, the inspection system 100 determines from one known point the location of any other point along the pipeline 140. According to another embodiment, the inspection system 100 determines the shape (i.e., curvature) of the pipeline 140.

Figure 2:
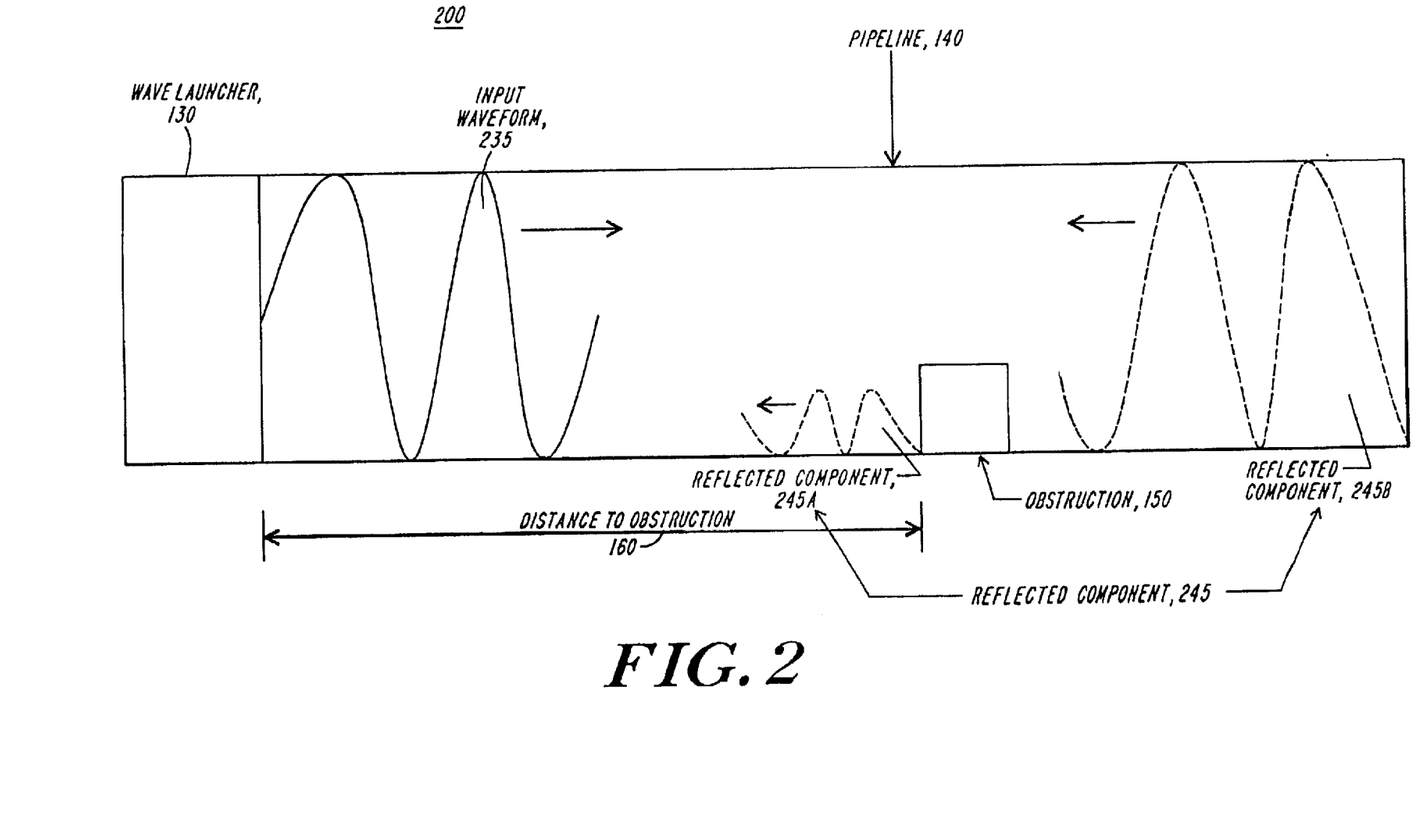
FIG. 2 is a conceptual diagram depicting illustrative waveforms transmitted from and received by an exemplary wave launcher used in the system of FIG. 1.

FIG. 2 is a conceptual diagram 200 depicting an illustrative input waveform 235 transmitted from the wave launcher 130, along with an exemplary reflected component 245. As depicted in FIG. 2, the analyzer 120 generates the input waveform 235 corresponding to a selected input energy. The analyzer 120 transmits the input waveform 235 to the wave launcher 130, and the wave launcher 130 then launches the input waveform 235 along the longitudinal central axis 142 of the pipeline 140. After sending the input waveform 235 into the pipeline 140, the wave launcher 130 receives a reflected component 245 of the input waveform 235. The reflected component 245 includes a reflected component 245A and a reflected component 245B. The reflected component 245A is the component of the input waveform 235 that the obstruction 150 reflects towards the wave launcher 130. The reflected component 245B is the component of the input waveform 235 that the end wall of the pipeline 140 reflects towards the wave launcher 130. The reflected component 245 of the input waveform 235 has a characteristic reflected energy that depends on the characteristics of the obstruction 150, the characteristics of the pipeline 140, the distance 160 between the wave launcher 130 and the obstruction 150, and other attributes of the illustrative inspection system 100 and pipeline 140. These dependencies are further described below.

Once the wave launcher 130 receives the reflected component 245 of the input waveform 235, the wave launcher 130 transfers it to the analyzer 120. The analyzer 120 determines the characteristic reflected energy of the reflected component 245 and transmits the reflected energy and the input energy to the processor 110. The processor 110 compares the input energy and reflected energy to determine the attributes of the obstruction 150. The attributes of the obstruction 150 may be any one of a variety of attributes, such as, but not limited to, the size of the obstruction 150, the type of the obstruction 150 (e.g., flange, rust, etc.), and the distance 160 to the obstruction 150. The processor 110 then reports its results on an output device connected to the processor 110.

According to a further feature, the illustrative processor 110 begins by calibrating the analyzer 120 for measurement.

In one embodiment, the processor 110 calibrates the analyzer 120 by temperature stabilizing the analyzer 120. Temperature stabilizing includes an operator of the illustrative system 100 positioning the analyzer 120 in a temperature cycling chamber. In one embodiment, the temperature cycling chamber is an enclosed, insulated area that introduces devices such as an analyzer 120 to a range of temperatures. The processor 110 is positioned outside of the temperature cycling chamber. The processor 110 loads from its processor memory (e.g., ROM, RAM) a test program at which the analyzer 120 can perform several functions and operations specified in the test program. For example, the processor 110 may request the analyzer 120 to perform the operations corresponding to the future operations that the analyzer 120 will carry out. Alternatively, the processor 110 may request the analyzer 120 to perform a diagnostic test on the components of the analyzer 120.

The processor 110 begins this test program and subsequently introduces the analyzer 120 to a range of temperatures while the analyzer 120 is in operation. Once the analyzer 120 is subjected to the entire range of temperatures, it becomes temperature stabilized and it transmits the results from the test program to the processor 110. The processor 110 receives and stores the results of the analyzer 120 running this test program. When the illustrative inspection system 100 is later positioned at the pipeline 140, the processor 110 measures the ambient temperature at the pipeline 140. The processor 110 consequently retrieves the stored results of the analyzer 120 in the temperature cycling chamber running the test program at the ambient temperature. The processor 110 initializes the analyzer 120 by using the stored results at the ambient temperature.

In another embodiment, the processor 110 calibrates the analyzer 120 every time the analyzer 120 is powered up. As described above, the processor 110 measures the ambient temperature of the pipeline 140 and executes the test program on the analyzer 120. The analyzer 120 executes the test program at the current temperature and then transfers the results to the processor 110. The processor 110 compares these results with expected results at the ambient temperature to obtain a temperature error associated with the analyzer 120. The processor 110 calibrates the analyzer 120 in this fashion every time the temperature at the location at which the illustrative inspection system 100 is used varies from the previous temperature at the previous location. Moreover, the processor 110 calibrates the analyzer 120 in this fashion whenever the analyzer 120 is powered down and then powered up. In a further embodiment, the processor 110 alerts the operator of the illustrative system 100 when the temperature error is above a predetermined temperature error threshold.

According to another embodiment, the processor 110 calibrates the analyzer 120 by temperature stabilizing the analyzer 120 in a thermostatically-controlled chamber. In one embodiment, the thermostatically-controlled chamber is a temperature cycling chamber, as described above, operating at a continuous, constant temperature. By way of example, the thermostatically-controlled chamber operates at 25° Celsius. The operator of the illustrative system 100 positions the analyzer 120 in the thermostatically-controlled chamber and the inspection system 100 begins normal execution. In a further embodiment, the processor 110 compares the output of the analyzer 120 at the constant temperature with expected results at the same constant temperature to obtain a temperature error associated with the analyzer 120. In still a further embodiment, the processor 110 displays a warning to the operator of the illustrative system 100 when the temperature error is above a predetermined temperature error threshold. Alternatively, the processor 110 initializes the analyzer 120 with one of the calibration techniques described above or below when the temperature error is above the predetermined threshold.

Once calibration is complete, the processor 110 instructs the analyzer 120 to generate an input waveform 235 that will be transmitted along the pipeline 140. The analyzer 120 may generate an input waveform 235 using a signal generator. Alternatively, the analyzer 120 applies a force to the pipeline 140 to generate a sound wave as the input waveform 235. The processor 110 indirectly selects the input energy of the input waveform 235 by selecting the frequency of the input waveform 235. Before transmitting the input waveform 235 to the wave launcher 130, the analyzer 120 determines the input energy associated with the input waveform 235.

As discussed in more detail below with respect to FIG. 6, after the analyzer 120 determines the input energy for to the input waveform 235, the analyzer 120 transmits the input waveform 235 to the wave launcher 130. The wave launcher 130 in turn launches the input waveform 235 along the central axis 142 of the pipeline 140. Then the wave launcher 130 receives the reflected component 245 of the input waveform 235 and sends it to the analyzer 120.

Once the analyzer 120 receives the reflected component 245, the analyzer 120 determines a transfer function relating the input energy corresponding to the input waveform 235 with the reflected energy corresponding to the reflected component 245 of the input waveform 235. The analyzer 120 determines a transfer function for each reflected component 245 (e.g., reflected component 245A and 245B) of the input waveform 235. The transfer function of energy is denoted by the following equation:

$$\text{transfer function} = \frac{E_{reflected}}{E_{input}}.$$

Once the analyzer 120 determines a transfer function for the input energy and the reflected energy corresponding to the reflected components 245A and 245B, it transmits these transfer functions to the processor 110.

Figure 3:
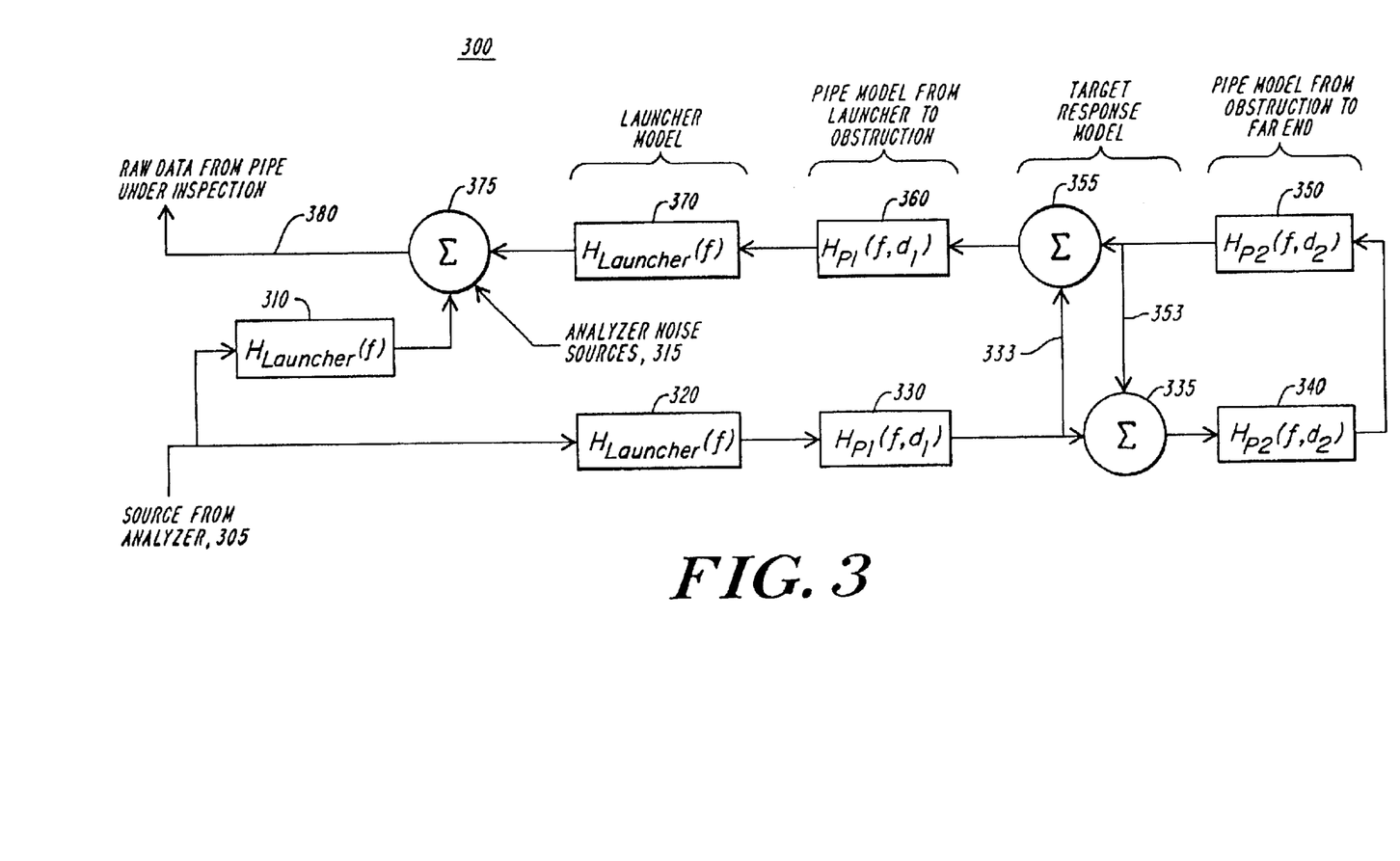
FIG. 3 depicts an equivalent model of the conceptual diagram of FIG. 1.

FIG. 3 depicts an equivalent model 300 of the illustrative inspection system 100 and the pipeline 140 of FIG. 1. The processor 110 determines the energy reflected from the obstruction 150 by generating a mathematically modeled pipeline that is representative of the pipeline 140. The analyzer 120 simulates the input waveform 235 that is transmitted along the pipeline 140 as a model input waveform 305. The model input waveform 305 is shown at the lower left corner of FIG. 3. The analyzer 120 transmits the model input waveform 305 to the wave launcher 130 in preparation for the launching of the model input waveform 305 along the central axis of the model pipeline. As a result of imperfections in test port cables and other calibration effects, a calibration component 310 of the model input waveform 305 is immediately reflected back to the analyzer 120. This calibration component 310 and the energy associated with this calibration component 310 is represented in FIG. 3 as $H_{Calibration}(f)$.

A first remainder 320 and a second remainder 330 of the model input waveform 305 are transmitted through the wave launcher 130 and travel the distance 160 to the model obstruction 335, or model target. The remainders 320 and 330 are represented in FIG. 3 as $H_{Launcher}(f)$ and $H_{P1}(f, d_1)$, respectively. The wave launcher 130 has intrinsic losses associated with it, and so when the model input waveform 305 is transmitted through the wave launcher 130 into the model pipeline, a reflected wave launcher portion 370 of the model input waveform 305 gets reflected toward the analyzer 120.

At the distance 160, the model obstruction 335 causes a first model reflected component 333 of the model input waveform 305 to be reflected toward the wave launcher 130. The first model reflected component 333 represents the reflected component 245A shown in FIG. 2. A third remainder 340 of the model input waveform 305 continues along the model pipeline until it reaches the end of the model pipeline. A second model reflected component 350 is then reflected toward the wave launcher 130 when it reaches the end wall of the model pipeline, and this second model reflected component 350 represents the reflected component 245B. The second model reflected component 350 and the energy corresponding to this reflected component 350 is represented in FIG. 3 by $H_{P2}(f, d_2)$. The sum of the model reflected components 333, 350 are combined at a first summation block 355 and the resulting sum 360 is transmitted to the analyzer 120. The resulting sum 360 is transmitted through the wave launcher 130, which is shown in FIG. 3 as $H_{P1}(f, d_1)$. Additionally, the model obstruction 335 reflects a portion of the second model reflected component 350 (that was reflected by the end wall of the model pipeline) back toward the end wall, creating a third model reflected component 353.

The wave launcher 130 transmits the resulting sum 360 and the reflected wave launcher portion 370 toward the analyzer 120. The resulting sum 360 and the reflected wave launcher portion 370 are combined with the calibration component 310 and any analyzer 120 noise sources 315 at a second summation block 375. A total model reflected component 380 is then transmitted to the analyzer 120. The total model reflected component 380 therefore includes a reflected component corresponding to the wave launcher 130 (e.g., reflected wave launcher portion 370), the model obstruction 335 (e.g., first model reflected component 333), the end wall of the model pipeline (e.g., second model reflected component 350), the calibration effects (e.g., calibration component 310), and any noise associated with the analyzer 120 (e.g., analyzer 120 noise sources 315).

As described in more detail below with respect to FIG. 6, the analyzer 120 receives the total model reflected component 380 and calculates a model transfer function relating the model input energy with the model reflected energy corresponding to the total model reflected component 380. The analyzer 120 then transfers this model transfer function to the processor 110. The processor 110 compares the transfer function associated with the reflected energy of the reflected component 245 to the model transfer function corresponding to the total model reflected component 380. From this comparison, the processor 110 determines the location 160 and size of the obstruction 150 and reports these results on an output device.

In one embodiment, the processor 110 includes the calibration component 310 of the analyzer 120, the response of the wave launcher 130, and the response of the pipeline 140 stored in its local memory (e.g., RAM, ROM). The analyzer 120 noise may be negligible if the pipeline 140 reflects most of the input waveform 235. In this situation, the processor 110 can detect a minute obstruction 150 at virtually unlimited range. In another embodiment, the processor 110 accounts for the analyzer 120 noise when the analyzer 120 receives the reflected component 245.

Illustratively, to process the calculations and modeling as described above, the processor 110 has digital signal processing capabilities that are used in a collection of DSP algorithms (discussed in further detail below). In one embodiment, the processor 110 uses an ideal lossless physics-based model as the hypothetical model to represent a pipeline 140 with no contaminants, defects, anomalies, or other losses. The model pipeline has uniform quality of construction material, an identical cross-section along the entire length of the model pipeline, and a perfectly conductive inner surface. Because the ideal physics-based model includes a model pipeline that is an ideal pipeline 140 with no losses, the processor 110 determines the response of the model pipeline and subsequently determines the type of the obstruction 150 and the location 160 of the obstruction 150 within the pipeline 140 by comparing the actual reflected energy of the pipeline 140 with the modeled reflected energy of the ideal pipeline 140. In another embodiment, the processor 110 uses an ideal lossy physics-based model. The processor 110 models the pipeline 140 using an ideal lossy physics-based model when the processor 110 assumes a conductive inner surface that experiences greater losses relative to the conductivity of the inner surface of the model pipeline.

Figure 4:
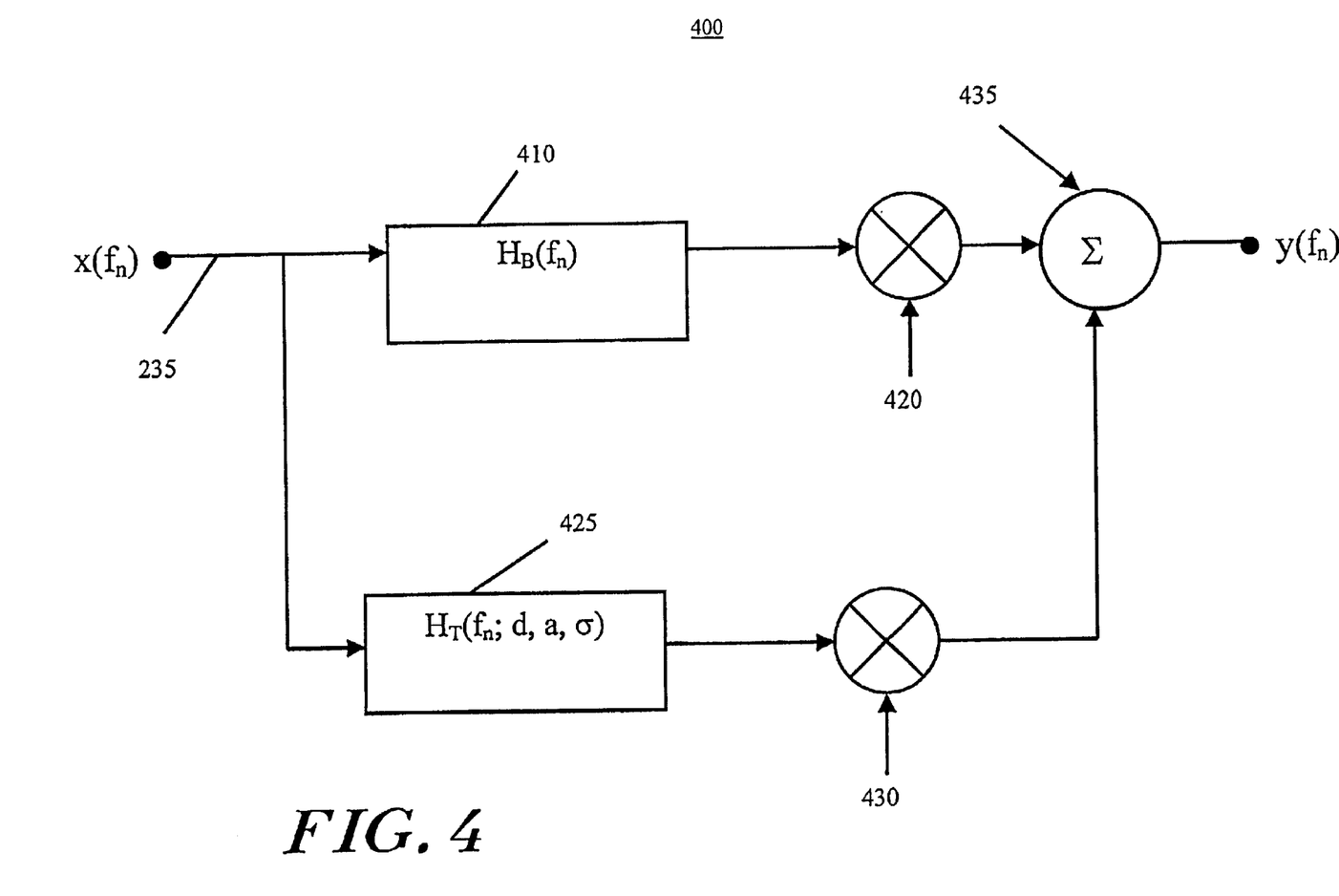
FIG. 4 is an illustrative block diagram showing a lossy physics-based model of the conceptual diagram of FIG. 1.

FIG. 4 is an illustrative block diagram showing a lossy physics-based system model 400 of the inspection system 100 incorporating partial a priori knowledge. As previously described, the analyzer 120 generates a series N of input waveforms 235 and applies these input waveforms 235 to the wave launcher 130. The amplitude $x(f_n)$, n=0,1, ..., N−1, of the input waveforms 235 is a function of the excitation frequency of the input waveform 235. The model 400 also includes the reflection response 410 of the wave launcher 130 and other near-field effects (i.e., the effects on the electric and magnetic fields of the reflected component 245 when the reflected component 245 is within the range of the wave launcher 130), denoted below by $H_B(f_n)$. The processor 110 represents partial knowledge of an as-built inspection system 100 in the reflection response 410 of the wave launcher 130. When reflected toward the wave launcher 130, the input waveform 235 further experiences a scaling coefficient 420 for near-field effects, represented below by $K_B$. The scaling coefficient 420 adjusts the magnitude and phase of the reflected component 245.

The processor 110 models the pipeline 140 as a lossy physics-based model 425, shown as $H_T(f_n; d, a, \sigma)$. The lossy physics-based model 425 of the pipeline 140 depends on several parameters of the pipeline 140, such as, but not limited to, the round-trip distance d between the obstruction 150 and the wave launcher 130, the radius a of the pipeline 140, the effective conductance σ of the pipeline's 140 inner surface, the scaling coefficient 430 $K_T$ for the obstruction 150, and the background noise 435 $\eta(f_n)$ of the analyzer 120.

For each of these input waveforms 235, the wave launcher 130 receives the reflected component 245 of each input waveform 235. The amplitude $y(f_n)$ of the reflected component 245 is also a function of the excitation frequency of the input waveform 235. The analyzer 120 calculates an estimate of the inspection system 100 transfer function, which, as described above, is given as:

$$H(f_n) = \frac{y(f_n)}{x(f_n)}. \quad (1)$$

The processor 110 then operates on this transfer function to locate and identify any obstructions 150 within the pipeline 140. Under the assumption that the background noise $\eta(f_n)$ is a zero-mean, independent complex Gaussian process, the processor 110 employs the minimum mean-squared error estimate, given as:

$$J_{\min} = \sum_{n=0}^{N-1} \left| H(f_n) - \hat{K}_B H_B(f_n) - \hat{K}_T H_T(f_n; \hat{d}, \hat{a}, \hat{\sigma}) \right|^2. \quad (2)$$

Note that, following standard convention, the carat (^) calls our attention to an estimated value of a parameter (as opposed to its "true" value).

To begin signal processing, the processor 110 assumes a range of distances over which to search for obstructions 150 within the pipeline 140. This range is denoted as $d_1$, $1=0,1, \ldots, L-1$, where L is the total number of steps within the range $d_1$ of distances at which to search for obstructions 150. In one embodiment, the range $d_1$ may cover a few kilometers in steps of 0.1 meters. For each value of $d_1$, the pipeline 140 transmission is calculated as:

$$H_T(f_n; d_1, a, \sigma) = e^{-\alpha_{11} d_1} e^{-j\beta_{11} d_1}, \quad (3)$$

where $$\alpha_{11} = \sqrt{\frac{2\pi f_n}{2\sigma}} \sqrt{\frac{(v'_{11})^4 + a^2(2\pi f_n)^2 \varepsilon_0 \mu_0 \left(1 - \left(\frac{v'_{11}}{2\pi f_n a \sqrt{\varepsilon_0 \mu_0}}\right)^2\right)}{a^3((v'_{11})^2 - 1)(2\pi f_n)^2 \varepsilon_0 \mu_0 \sqrt{1 - \left(\frac{v'_{11}}{2\pi f_n a \sqrt{\varepsilon_0 \mu_0}}\right)^2}}}, \text{ and} \quad (4)$$

$$\beta_{11} = 2\pi f_n \sqrt{\varepsilon_0 \mu_0} \sqrt{1 - \left(\frac{v'_{11}}{2\pi f_n a \sqrt{\varepsilon_0 \mu_0}}\right)^2}. \quad (5)$$

In Equations (4) and (5), the new symbols are identified as:

$\varepsilon_0$ Permittivity of free space, $8.854 \times 10^{-12} \frac{C^2}{N \cdot m^2}$, $\mu_0$ Permeability of free space, $4\pi \times 10^{-7} \frac{Wb}{A \cdot m}$, Given the three vectors, $H(f_n)$, $H_B(f_n)$, $H_T(f_n; d_1, \hat{a}, \hat{\sigma})$, the processor 110 calculates the inter- and intra-signal correlation functions as:

$$R_{HH} = \sum_{n=0}^{N-1} H^*(f_n) H(f_n), \quad (6)$$

$$R_{H_B H_B} = \sum_{n=0}^{N-1} H_B^*(f_n) H_B(f_n), \quad (7)$$

$$R_{H_T H_T} = \sum_{n=0}^{N-1} H_T^*(f_n; d_l, a, \sigma) H_T(f_n; d_l, a, \sigma), \quad (8)$$

$$R_{H_B H_T} = \sum_{n=0}^{N-1} H_B^*(f_n) H_T(f_n; d_l, a, \sigma), \quad (9)$$

$$R_{H_T H_B} = \sum_{n=0}^{N-1} H_T^*(f_n; d_l, a, \sigma) H_B(f_n), \quad (10)$$

and the measurement correlation functions as:

$$P_{H_B} = \sum_{n=0}^{N-1} H_B^*(f_n) H(f_n), \quad (11)$$

$$P_{H_T} = \sum_{n=0}^{N-1} H_T^*(f_n; d_l, a, \sigma) H(f_n). \quad (12)$$

The signal correlation functions are used to form the correlation matrix $$R(d_l) \equiv \begin{bmatrix} R_{H_B H_B} & R_{H_B H_T} \\ R_{H_T H_B} & R_{H_T H_T} \end{bmatrix}, \quad (13)$$

while the measurement correlation functions are incorporated into the vector $$p(d_l) \equiv \begin{bmatrix} P_{H_B} \\ P_{H_T} \end{bmatrix}. \quad (14)$$

For a particular selection of distance $d_1$, the minimum mean-squared error is given as:

$$J_{min}(d_1) = R_{HH} - p^H R^{-1} p. \quad (15)$$

The associated values of the optimum scaling constants are given as $$\begin{bmatrix} K_B(d_l) \\ K_T(d_l) \end{bmatrix} = R^{-1} p. \quad (16)$$

Equations (15) and (16) are computed for all $d_1$, $l=0,1,\ldots,L-1$. Once completed, the global minimum attained by $J_{min}$ is identified together with the distance $d_1$ at which it occurs, and the attendant value of $K_T$. The magnitude of the estimate of $K_T$ is related to the cross-sectional area of the obstruction 150 as:

$$|K_T| \approx 8.3 \times T^2 + 0.5 \times T, \quad (17)$$

where T is the fractional cross-sectional area of the obstruction 150. This expression is inverted to find the size of the target 150.

To find the type of the obstruction 150, the magnitude of $J_{min}$ at its global minimum helps define the depth (i.e., distance 160 along the length of the pipeline 140) of the obstruction 150. For example, since the processor 110 bases the lossy physics-based model 425 on the presumption of an obstruction 150 having "zero thickness," an obstruction 150 of substantial length provides a relatively high value at the local minimum. In one embodiment, the processor 110 displays the magnitude of $J_{min}$ at its global minimum to the user of the system 100 so that the user can determine the type of the obstruction 150. In another embodiment, the processor 110 has a table stored in local memory associating a range of depths with a type of obstruction 150 and determines the type of obstruction 150 from the depth and the stored table.

Since $J_{min}$ is calculated as a function of distance (see Equation 15), the processor 110 determines the location 160 of the obstruction 150 from the distance $d_1$. The distance $d_1$ at which the global minimum of $J_{min}$ occurs is the maximum likelihood estimate of the target 150 location 160 from the wave launcher 130.

In an alternate embodiment, the processor 110 employs the method of maximum likelihood, which requires full knowledge of the output probability density functions, to locate and identify any and all obstructions 150 within the pipeline 140. The description provided above is strictly illustrative and does not make pretense to describe the myriad of improvements possible or the field of alternatives available.

As skilled artisans will appreciate, the processor 110 may be any one of a variety of devices, such as, but not limited to, a laptop computer with digital signal capabilities, a personal digital assistant with digital signal capabilities, a mobile telephone with digital signal capabilities, and a beeper with digital signal capabilities. Generally, the processor 110 can be any device that has computer memory (e.g., RAM, ROM) and digital signal processing capabilities so that the DSP algorithms can be stored and executed on the processor 110.

In another embodiment, the processor 110 uses an average model of the entire pipeline 140. The processor 110 averages losses associated with construction, internal characteristics, differences within the cross section, and other losses apparent throughout the pipeline 140 to obtain an average model pipeline. In yet another embodiment, the processor 110 utilizes a section by section model of the pipeline 140, in which the processor 110 segments the pipeline 140 into sections and computes a representation for each of the segmented sections. The processor 110 builds a model of a portion of the pipeline 140 being tested by analyzing and then joining each section of the relevant portion of the pipeline 140.

According to one embodiment, the operator of the inspection system 100 selects the appropriate model (e.g., ideal physics-based system model 400, average model, section-by-section model) that the processor 110 uses to model the pipeline 140 from a menu displayed on the output device, as discussed more fully below. According to another embodiment, the processor 110 determines which model to apply depending on the characteristics of the pipeline 140. As described in more detail below with respect to FIG. 6, after the processor 110 receives the transfer function relating the input energy corresponding to the input waveform 235 with the reflected energy corresponding to the reflected component 245, the processor 110 uses this data to determine which model to use in determining the characteristics of the obstruction 150.

Figure 5:
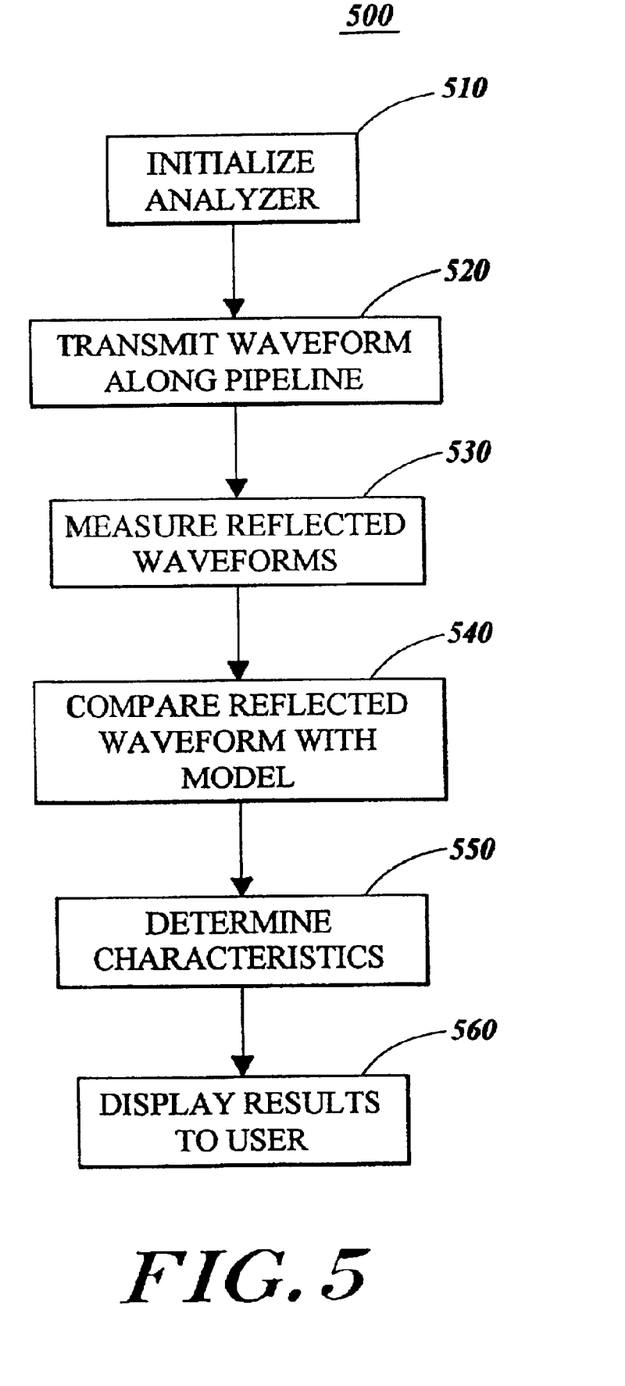
FIG. 5 is a flow diagram depicting an illustrative operation of the system of FIG. 1.

FIG. 5 is a flow diagram 500 depicting an illustrative operation of the inspection system 100 of FIG. 1. First, the processor 110 initializes (Step 510) the analyzer 120. In one embodiment and as described above, the processor 110 calibrates the analyzer 120 by temperature stabilizing the analyzer 120. The processor 110 may also initialize the analyzer 120 by additionally or exclusively performing a diagnostic check on the components of the analyzer 120, which are described further in FIG. 6. In another embodiment, the processor 110 initializes the analyzer 120 by supplying power to the analyzer 120. Initialization may also include a combination of the techniques described above.

At step 520, the wave launcher 130 transmits the input waveform 235 along the central longitudinal axis 142 of the pipeline 140. As described above, the analyzer 120 generates the input waveform 235 and transmits it to the wave launcher 130. More specifically, in one embodiment the input waveform 235 is an electromagnetic waveform having a selected frequency and energy. The range of frequencies at which the input waveform 235 is generated is discussed more fully below with respect to FIG. 6. As skilled artisans will appreciate and as described more fully below, the input waveform 235 may be any one of a variety of wideband waveforms, such as, but not limited to, a chirp waveform, a spread spectrum waveform, a wavelet waveform, and a solitons waveform. In another embodiment, the input waveform 235 is not an electromagnetic waveform but rather is an acoustic waveform.

After the wave launcher 130 transmits the input waveform 235 along the central longitudinal axis 142 of the pipeline 140, the wave launcher 130 receives the reflected component 245 of the input waveform 235 and transmits it to the analyzer 120. As described above with respect to FIG. 2, the analyzer 120 measures (Step 530) the characteristic reflected energy of the reflected component 245. The analyzer 120 then determines the transfer function relating the input energy corresponding to the input waveform 235 with the reflected energy corresponding to the reflected component 245 (e.g., reflected components 245A and 245B) of the input waveform 235. The analyzer 120 then transmits the transfer function to the processor 110.

As discussed with respect to FIG. 3, the processor 110 compares (Step 540) the transfer function associated with the reflected energy of the reflected component 245 with the model transfer function corresponding to the total model reflected component 380. From this comparison, the processor 110 determines (Step 550) the location 160 and size of the obstruction 150. Although the flow diagram 500 illustrates the operation of the inspection system 100 for one obstruction 150, the invention extends to a pipeline 140 containing a plurality of obstructions 150. In other embodiments, step 550 may also include using the above discussed mathematical process to determine the axial shape of the pipeline 140 (i.e. the curvature of the pipeline 140 along the central longitudinal axis 142. Skilled artisans will appreciate that the pipeline 140 need not have a circular cross-section 144 and that the location of the central axis 142 along which the input waveform 235 propagates may be adjusted to accommodate pipelines 140 having non-circular cross-sections 144. As previously mentioned, in some embodiments, a user provides the measurement system 100 of the invention with cross-sectional information of the pipeline 140. However, according to other embodiments, the system 100 automatically determines the cross-section 144 of the pipeline 140.

At step 560, the processor 110 displays the results on an output device to the user of the inspection system 100. The reported results may be any of one of a variety of statistics, such as, but not limited to, the type of the obstruction 150, the size of the obstruction 150, and the location 160 of the obstruction 150. Examples of output devices are any one of a variety of devices such as, but not limited to, a computer monitor, a LCD screen, one or several light sources having a predefined meaning associated with the obstruction 150 (e.g., a blue light denoting that the obstruction 150 is a flange, a red light indicating that the obstruction 150 is rust, etc.), a cellular phone screen, a personal digital assistant screen, and an output device that generates predefined tones (e.g., a 40 Hz tone meaning the obstruction 150 is a flange, a 60 Hz tone meaning the obstruction 150 is rust, etc.).

In one embodiment, the processor 110 displays the results corresponding to the obstruction 150 with a graphical user interface (GUI). The output device associated with the processor 110 displays the GUI, and the GUI may represent the obstruction 150 with images, buttons, scales, etc. Alternatively, the processor 110 displays the results with an echo plot, which is a plot that displays points to trace the location 160 and size of the obstruction 150 in the pipeline 140. In yet another embodiment, the processor 110 displays the results with a textual description. For example, the processor 110 reports that the obstruction 150 is a "3 cm buckle found at 10 km". The processor 110 may also report the results with a 3-dimensional solids rendering plot. Although several techniques to output the results are described above, skilled artisans will realize that other output methods may be used in place of or in combination with the above techniques.

Figure 6:
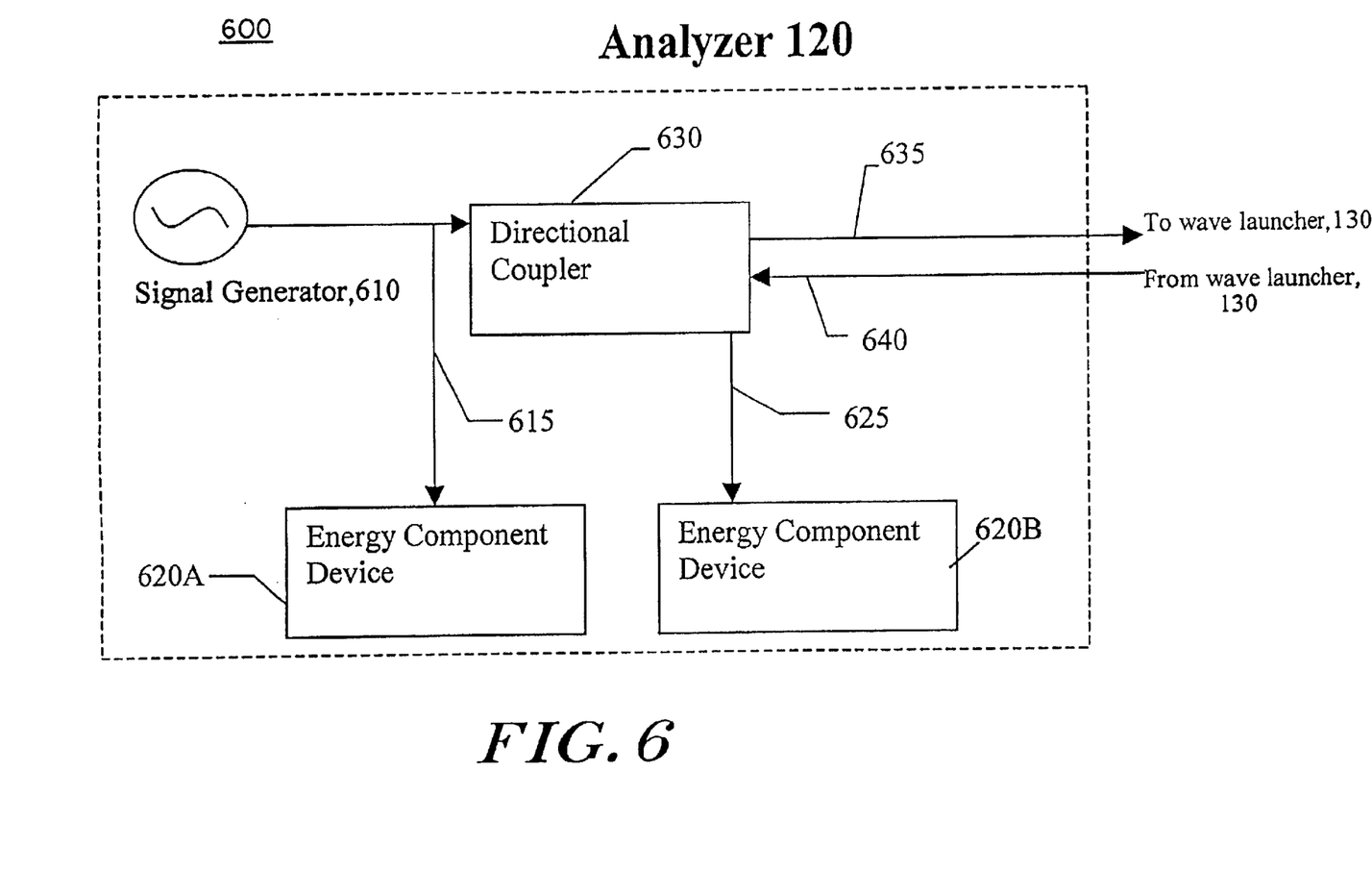
FIG. 6 is a more detailed block diagram of the illustrative analyzer of FIG. 1.

FIG. 6 is a more detailed block diagram 600 of the illustrative analyzer 120 of FIG. 1. In one embodiment, the analyzer 120 is an automated vector network analyzer. The analyzer 120 includes a signal generator 610, energy component devices 620A and 620B, and a directional coupler 630. The directional coupler 630 transmits an input energy 615 associated with the input waveform 235 to the energy component device 620A. The directional coupler 630 transmits a reflected energy 625 associated with the reflected component 245 to the energy component device 620B. The directional coupler 630 transmits the input waveforms 235 to the wave launcher 130 along a first communication channel 635. The wave launcher 130 transmits the reflected component 245 of the input waveform 235 to the analyzer 120, and more specifically to the directional coupler 630, along a second communication channel 640.

The signal generator 610 generates the input waveform 235 that is transmitted along the pipeline 140. The signal generator 610 generates input waveforms 235 having a frequency within a certain range of frequencies, determined by the characteristics of the signal generator 610 and by the characteristics of the pipeline 140. As described above, the pipeline 140 acts as a waveguide for the input waveform 235, and input electromagnetic waveforms 235 propagate along a waveguide with different field configurations (e.g., electric field and magnetic field) and different velocities. This is referred to as the mode of the wave, and different modes of a wave can propagate along a waveguide simultaneously.

The pipeline 140 has a cutoff frequency below which no input waveform 235 will propagate. This cutoff frequency is the minimum frequency needed to propagate the first mode of the input waveform 235 along the pipeline 140. The first mode of an electromagnetic waveform, which propagates along the pipeline 140 alone, is called the dominant mode of the waveguide. The minimum frequency at which the dominant mode exists, which is the cutoff frequency, depends on the cross-section 144 of the opening of the pipeline 140. The maximum frequency at which the dominant mode exists depends on the characteristics of the pipeline 140.

In one embodiment, the pipeline 140 is a circular cylindrical pipeline 140, and the range of frequencies at which the dominant mode propagates is given by the following relationship:

$$\frac{K_1 c}{a} < f_d < \frac{K_2 c}{a}$$

wherein:
$f_d$ is the frequency at which the dominant mode propagates along the pipeline 140;
c is the speed of light ($2.998 \times 10^8$ meters/second);
$K_1$ and $K_2$ are constants associated with the characteristics of the pipeline 140; and
a is the radius of the circular cross-section 144 of the pipeline 140.

For a circular cylindrical pipeline 140, the dominant mode is referred to as the $TE_{11}$ mode. TE waves are waves in which the longitudinal components of the electric field at the walls of the waveguide are zero and the longitudinal magnetic field is non-zero. In one embodiment, the signal generator 610 transmits the dominant mode of the input waveform 235. The illustrative signal generator 610 generates an input waveform 235 for the entire range of frequencies at which the dominant mode exists. When the input waveform 235 is at a frequency associated with the dominant mode, the analyzer 120 generates a unique transfer function relating the input energy 615 and the reflected energy 625. The transfer function is unique because the dominant mode is the only mode of the input waveform 235 that propagates along the pipeline 140.

According to one illustrative embodiment, the user of the inspection system 100 enters the diameter information for the pipeline 140 into the processor 110. According to another embodiment, the user enters the shape and dimensions of the cross-section 144 of the pipeline 140 into the processor 110. The processor 110 uses the entered information to determine the frequency range at which the dominant mode of the input waveform 235 propagates. The processor 110 then notifies the analyzer 120 to generate input waveforms 235 each having a frequency within the range of frequencies of the dominant mode. Alternatively, the user of the inspection system 100 enters the brand name of the pipeline 140 and the processor 110 uses this data to retrieve from its local memory the cross-sectional information of the pipeline 140. Generally, the user of the inspection system 100 can input any parameter of the pipeline 140 into the processor 110 as long as the processor 110 can determine the frequency range of the dominant mode of the pipeline 140.

In one embodiment and as briefly described above with respect to FIG. 5, the analyzer 120 generates a chirp waveform as the input waveform 235. A chirp waveform is a quasi-sinusoidal waveform that has the property that its instantaneous frequency is a linear function of time. The analyzer 120 generates discrete chirp waveforms and increments the frequency of the input waveform 235 by a step-size through a range of sinusoidal frequencies. By way of example, the analyzer 120 generates discrete chirp waveforms and increments the frequency by a step-size of 1 Hz through 3 Hz (i.e., the analyzer 120 generates discrete chirp waveforms having a frequency of 600 MHz, 601 MHz, and 602 MHz).

In another embodiment and as briefly described above with respect to FIG. 5, the analyzer 120 generates a prototype waveform and derives a wavelet waveform as the input waveform 235. The analyzer 120 derives a wavelet waveform by stretching or delaying the prototype waveform. The analyzer 120 has a high degree of control over the joint time and frequency distribution of the input energy 615 in the wavelet waveform. For example, a wavelet waveform can be derived such that all frequency components arrive at substantially the same time and substantially in phase.

In another embodiment, the analyzer 120 generates a spread spectrum waveform as the input waveform 235. The spread spectrum waveform reduces interference by spreading the input waveform 235 in bandwidth prior to transmission along the pipeline 140. Upon receiving the reflected component 245 of the input waveform 235, the analyzer 120 despreads, or decreases, the bandwidth of the reflected component 245 by the same amount of bandwidth as the increase. This technique in turn decreases the effect of the interference that occurs during the transmission and reception of the input waveform 235 and the reflected component 245.

When the wave launcher 130 launches many input waveforms 235 of different frequencies within the range of frequencies of the dominant mode, each input waveform 235 travels along the central axis 142 of the pipeline 140 at different velocities due to the different frequencies. This is referred to as "dispersion" of the input waveform 235. When the pipeline 140 is a relatively straight pipeline 140, the operation of the inspection system 100 is not affected by the different velocities of the input waveforms 235 because each input waveform 235 has a separate component 245 of the input waveform 235 reflected toward the wave launcher 130 at different times corresponding to the different velocities. Therefore, the inspection system 100 detects the obstruction 150 when the input waveform 235 disperses in a straight pipeline 140.

In another embodiment, the pipeline 140 is a pipeline 140 that has curves and bends. As previously described above, the user of the inspection system 100 may provide information such as cross-sectional and axial curvature information to the processor 110. The processor 110 uses this information to calculate the range of frequencies corresponding to the dominant mode as well as the range of frequencies corresponding to higher order modes of the input waveform 235 and to generate a mathematical model of the pipeline 140. Alternatively, the system 100 determines the cross-sectional and axial curvature properties of the pipeline 140. Either way, in one embodiment the signal generator 610 generates input waveforms 235 within a range of frequencies that correspond to more than one mode of the input waveform 235 (i.e., the dominant mode and higher order modes). The wave launcher 130 then launches these input waveforms 235 along the central axis 142 of the curved pipeline 140. The analyzer 120 receives an independent reflected energy 625 along the second communication channel 640 for each input waveform 235 that was introduced.

In one embodiment and as described above, the processor 110 compensates for dispersion in its formulation of the model pipeline and therefore forces time-alignment of all the frequencies of the input waveforms 235 that travel at different velocities. The pipeline 140 incorporates dispersion into its DSP algorithms to model the pipeline 140 because the dominant mode dispersion of an input waveform 235 is substantially identical in both a straight and curved pipeline 140. For example, the lossy physics-based model 425 described above compensates for dispersion. More specifically, the lossy physics-based model 425 described above incorporates dispersion in its formulation of the model pipeline with the term under the second radical in Equation (5).

In another embodiment, the processor 110 uses the transfer function of each input waveform 235 to determine which model (ideal physics-based system model 400, average model, section-by-section model) of the pipeline 140 to use. Therefore, the analyzer 120 helps the processor 110 accurately model the pipeline 140 when the analyzer 120 generates higher order mode input waveforms 235 for a curved pipeline 140.

The processor 110 models the curves in a pipeline 140 more realistically as the number of modes that are propagating increases because of dispersion, which was described above. As the frequency of the input waveforms 235 increases, and therefore higher order modes propagate, the input waveforms 235 propagate around curves with greater differences in velocities relative to the difference in velocities along a relatively straight portion of the pipeline 140. The processor 110 models the curves more accurately due to these velocity differences. Therefore, the inspection system 100 detects the obstruction 150 when the pipeline 140 is a curved pipeline 140.

In another embodiment and as briefly described above with respect to FIG. 5, the analyzer 120 generates a soliton waveform as the input waveform 235. A soliton waveform is a class of waveforms designed to pass through a non-linear dispersive media without losing its shape and properties. The processor 110 uses soliton waveforms as the input waveform 235 to characterize the curvature of the pipeline 140. In one illustrative approach, the processor 110 determines the curvature of the pipeline 140 by refining the shape of the soliton waveform in real-time until the analyzer 120 receives an unchanged reflected component 245. Alternatively, the processor 110 refines the spectral content of the soliton waveform in real-time until the analyzer 120 receives an unchanged reflected component 245. In another embodiment, the processor 110 refines the power level of the soliton waveform in real-time until the analyzer 120 receives an unchanged reflected component 245.

In another embodiment, the pipeline 140 is a hollow rectangular pipeline 140, and the dominant mode of the input waveform 235 propagates over the range of frequencies given by the following relationship:

$$\frac{c}{2a} < f_d < \frac{c}{2b}$$

wherein:

$f_d$ is the frequency at which the dominant mode will propagate along the rectangular pipeline 140;
c is the speed of light ($2.998 \times 10^8$ meters/second);
a is the height of the pipeline 140; and
b is the width of the pipeline 140, assuming the width is less than the height of the pipeline 140.

According to this embodiment, the user of the inspection system 100 provides the processor 110 with the height and width of the pipeline 140. With these parameters, the processor 110 determines the range of frequencies at which the dominant mode and higher order modes of the input waveform 235 propagate along the hollow rectangular pipeline 140.

The energy component devices 620A, 620B extract out the magnitude and phase components of the input energy 615 and the reflected energy 625 associated with the input waveform 235 and the reflected component 245, respectively. The processor 110 requires the magnitude and phase of the input energy 615 and the reflected energy 625 to determine the attributes of the obstruction 150. The energy component devices 620A and 620B do not affect the input waveform 235, the reflected component 245, the input energy 615, or the reflected energy 625 when extracting out the magnitude and phase of the input energy 615 and the reflected energy 625.

The directional coupler 630 transmits and receives energy between the signal generator 610, the energy component device 620B, and the wave launcher 130 without any physical connection between the devices. In one embodiment, the directional coupler 630 uses the electric fields generated by the circuits of these components to transmit and receive energy.

According to a further embodiment, the inspection system 100 detects the axial curvature of the pipeline 140 with or without an obstruction 150. As described above, the wave launcher 130 launches input waveforms 235 corresponding to the dominant mode and higher order modes of the input waveforms 235 along the central axis 142 of the pipeline 140.

The axial curvature of the pipeline 140 may be useful to the user of the inspection system 100 for a variety of reasons. By way of example, it can be useful to determine a change in the degree of curvature over a period of time and to locate the end wall of the pipeline 140 when the end wall is not located at the expected location, and the like. The change in the degree of curvature over a period of time also shows, for instance, a portion of the pipeline 140 experiencing a greater amount of force applied to it relative to less curved portions. The user can use the curvature information to adjust characteristics of the pipeline 140 such as re-position the pipeline 140 in a modified location, pad the curved portion of the pipeline 140 to adjust (i.e., decrease) the amount of force applied to it, apply a similar force to the uncurved portions of the pipeline 140 to decrease the rate of curvature change along the pipeline 140, or the like. In yet another embodiment, knowing an initial location point along the pipeline 140 and curvature information determined by the inspection system 100, a user of the inspection system 100 can map the location of a length of pipeline 140, even if the pipeline 140 is underground or submerged underwater.

The location of any point along the pipeline 140, such as the point corresponding to the end wall of the pipeline 140, may be useful to the user of the inspection system 100 for a variety of reasons. For example, a user of the inspection system 100 may know the location of a point along the pipeline 140 but may not know the location of the end wall of the pipeline 140 if the pipeline 140 is laid underground or underwater. Similarly, although a user of the inspection system 100 may know the starting point of an old pipeline 140 buried in the foundation of a building, a user may not know the path the pipeline 140 takes throughout the foundation. One skilled in the art will appreciate that knowing the location of an entire segment of pipeline 140 may, for example, aid in repair of an anomaly 150. Such information may also be helpful with regard to installing additional pipeline 140 segments.

Figure 7:
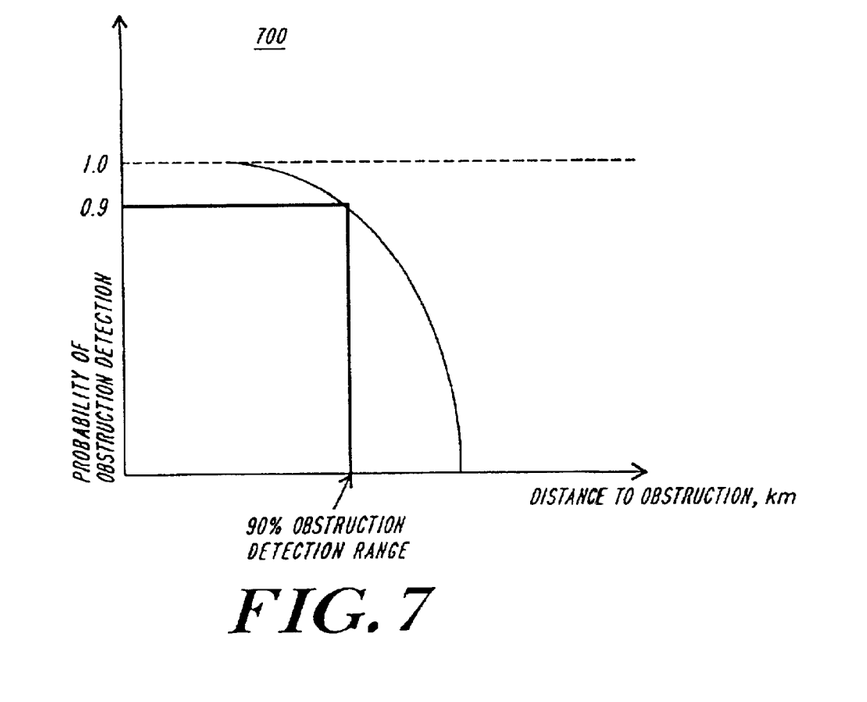
FIG. 7 depicts a graph describing a probability that a single anomaly will be detected using the illustrative system of FIG. 1 as the distance between the anomaly and the system of FIG. 1 increases.

FIG. 7 shows a graph 700 describing the probability that the inspection system 100 detects the obstruction 150, as the distance 160 between the obstruction 150 and the wave launcher 130 increases. The graph 700 describes the probability that the inspection system 100 detects the obstruction 150 in a straight pipeline 140 or a curved pipeline 140. For example, the graph 700 represents the probability that the inspection system 100 detects the obstruction 150 in a straight pipeline 140 when the input waveforms 235 propagate at frequencies corresponding to the dominant mode. The graph 600 also represents the probability that the inspection system 100 detects the obstruction 150 in a curved pipeline 140 when the input waveforms 235 propagate at frequencies corresponding to more than one mode of the input waveform 235.

Figure 8:
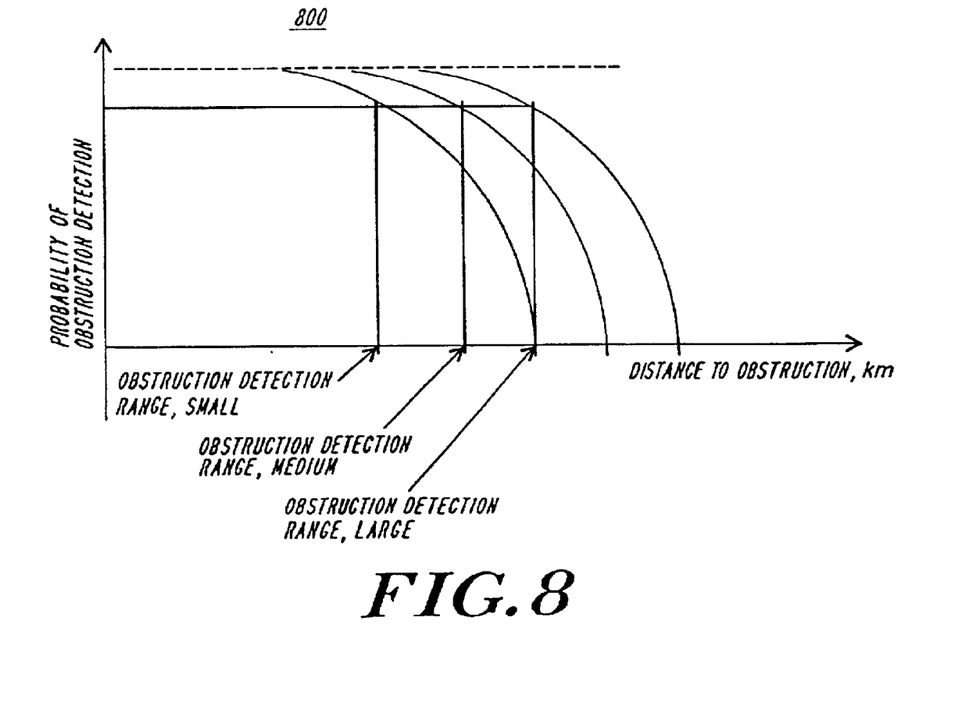
FIG. 8 is a graph portraying a probability that a single anomaly of varied sizes (small, medium, large) will be detected using the illustrative system of FIG. 1 as the distance between the anomaly and the system increases.

FIG. 8 is a graph illustrating the probability that the inspection system 100 detects a single obstruction 150 as the size (e.g., small, medium, large) of the obstruction 150 varies. The amplitude of the reflected component 245 increases as the size of the obstruction 150 increases. Therefore, the probability of detection generally increases as the size of the obstruction 150 increases. This increase is represented by translating the left curve shown in FIG. 8 to the right as the size of the target 150 increases.

The inspection system 100 may be embodied in other specific forms without departing from the spirit or essential characteristics of the claimed invention. The foregoing embodiments are therefore to be considered in all respects illustrative rather than limiting on the present invention.

What is claimed is:

1. A pipeline inspection system comprising, a wave launcher in communication with a pipeline and adapted to transmit an input waveform having a selected input energy along a longitudinal axis inside said pipeline, and to receive a reflected component of said input waveform from said pipeline, said reflected component having a characteristic reflected energy, an analyzer in communication with said wave launcher and adapted to generate said input waveform, and to receive said reflected component of said input waveform from said wave launcher, and a processor in communication with said analyzer and adapted to compare said input waveform with said reflected component of said input waveform to determine a characteristic of said pipeline, wherein the wave launcher, the analyzer, and the processor operate in a fashion that is non-invasive to the pipeline.

2. The apparatus of claim 1, wherein said processor is further adapted to compare said input waveform with said reflected component to detect an anomaly in said pipeline.

3. The apparatus of claim 1, wherein said processor is further adapted to compare said input waveform with said reflected component to determine an axial curvature in said pipeline.

4. The apparatus of claim 1, wherein said processor is further adapted to compare said input waveform with said reflected component to determine location points along said pipeline relative to an initial known location.

5. The apparatus of claim 1, wherein said wave launcher further comprises a probe antenna, said probe antenna adapted for transmitting said input waveform into said pipeline.

6. The apparatus of claim 1, wherein said analyzer is further adapted to detect said reflected component along said longitudinal axis of said pipeline.

7. The apparatus of claim 1, wherein said processor is further adapted to generate a mathematical model representative of said pipeline.

8. The apparatus of claim 1, wherein said analyzer is further adapted to extract a characteristic energy and phase for said input waveform and said reflected component.

9. The apparatus of claim 1, wherein said analyzer is further adapted to generate said input waveform with a frequency above a characteristic cutoff frequency of said pipeline.

10. The apparatus of claim 1, wherein said analyzer is further adapted to generate said input waveform at a frequency within a range of frequencies for which a dominant mode for said pipeline exists.

11. The apparatus of claim 1, wherein said analyzer is further adapted to generate an electromagnetic waveform as said input waveform.

12. The apparatus of claim 1, wherein said analyzer is further adapted to generate an acoustic waveform as said input waveform.

13. The apparatus of claim 1, wherein said analyzer is further adapted to generate said input waveform as one of a spread spectrum waveform, a chirp waveform, and a soliton waveform.

14. The apparatus of claim 1, wherein said analyzer is further adapted to generate said input waveform as wideband waveform.

15. The apparatus of claim 1 further comprising calibration elements adapted to temperature stabilize said analyzer.

16. The apparatus of claim 2, wherein said anomaly is at least one of a crack, a corrosion, a leak, a location of an end wall, an obstruction, a flange, a weld, and a restriction in said pipeline.

17. The apparatus of claim 2, wherein said processor is further adapted to compare said input waveform with said reflected component to determine a location of said anomaly in said pipeline.

18. The apparatus of claim 2, wherein said processor is further adapted to compare said input waveform with said reflected component to determine a shape of said anomaly in said pipeline.

19. The apparatus of claim 2, wherein said processor is further adapted to compare said input waveform with said reflected component to determine one of an absolute size of said anomaly and a relative size of said anomaly relative to an internal diameter of said pipeline.

20. The apparatus of claim 5, wherein said probe antenna of said wave launcher is in physical contact with said pipeline.

21. The apparatus of claim 7, wherein said mathematical model is ideal.

22. The apparatus of claim 7, wherein said mathematical model is lossy.

23. The apparatus of claim 7, wherein said mathematical model is one of an averaging model and a cross-sectional model.

24. The apparatus of claim 7, wherein said processor is further adapted to generate a model transfer function relating a model input waveform to a model reflected component, an actual transfer function relating an actual input waveform to an actual reflected component, and to determine said characteristic at least in part by comparing said model transfer function with said actual transfer function.

25. The apparatus of claim 7, wherein said processor is further adapted to determine said characteristic of said pipeline at least in part by comparing an actual reflected component with a model reflected component.

26. The apparatus of claim 10, wherein said input waveform comprises a plurality of input signals within said range of frequencies.

27. The apparatus of claim 26, wherein said analyzer is further adapted to detect differences in velocity between said plurality of input signals as said input signals propagate in said pipeline, and said processor is further adapted to determine a curvature of said pipe along said longitudinal axis from said differences in velocity.

28. The apparatus of claim 26, wherein said analyzer is further adapted to detect differences in velocity between reflected components of each of said plurality of input signals to determine a curvature of said pipeline along said longitudinal axis.

29. A method of inspecting a characteristic of a pipeline, said method comprising, transmitting an input waveform having a selected input energy along a longitudinal axis inside said pipeline, receiving a reflected component of said input waveform from said pipeline, said reflected component having a characteristic reflected energy, and comparing said input waveform with said reflected component of said input waveform to determine said characteristic of said pipeline, wherein the transmitting, receiving, and comparing steps occur in a fashion that is non-invasive to the pipeline.

30. The method of claim 29 further comprising, comparing said input waveform with said reflected component to detect an anomaly in said pipeline.

31. The method of claim 29 further comprising, comparing said input waveform with said reflected component to determine an axial curvature in said pipeline.

32. The method of claim 29 further comprising, comparing said input waveform with said reflected component to determine location points along said pipeline relative to an initial known location.

33. The method of claim 29, further comprising, detecting said reflected component along said longitudinal axis of said pipeline.

34. The method of claim 29 further comprising, generating a mathematical model representative of said pipeline.

35. The method of claim 29 further comprising, extracting a characteristic energy and phase for said input waveform and said reflected component.

36. The method of claim 29 further comprising, generating said input waveform with a frequency above a characteristic cutoff frequency of said pipeline.

37. The method of claim 29 further comprising, generating said input waveform at a frequency within a range of frequencies for which a dominant mode for said pipeline exists.

38. The method of 29 further comprising, generating an electromagnetic waveform as said input waveform.

39. The method of claim 29 further comprising, generating an acoustic waveform as said input waveform.

40. The method of claim 29 further comprising, generating said input waveform as one of a spread spectrum waveform, a chirp waveform, and a soliton waveform.

41. The method of claim 29 further comprising, generating said input waveform as a wideband waveform.

42. The method of claim 29 further comprising, calibrating said analyzer to be temperature stable.

43. The method of claim 30, wherein said anomaly is at least one of a crack, a corrosion, a leak, a location of an end wall, an obstruction, a flange, a weld, and a restriction in said pipeline.

44. The method of claim 30 further comprising, comparing said input waveform with said reflected component to determine a location of said anomaly in said pipeline.

45. The method of claim 30 further comprising, comparing said input waveform with said reflected component to determine a shape of said anomaly in said pipeline.

46. The method of claim 30 further comprising, comparing said input waveform with said reflected component to determine one of an absolute size of said anomaly and a relative size of said anomaly relative to an internal diameter of said pipeline.

47. The method of claim 34, wherein said mathematical model is ideal.

48. The method of claim 34, wherein said mathematical model is lossy.

49. The method of claim 34, wherein said mathematical model is one of an averaging model and a cross-sectional model.

50. The method of claim 34 further comprising, generating a model transfer function relating a model input waveform to a model reflected component, an actual transfer function relating an actual input waveform to an actual reflected component, and to determine said characteristic at least in part by comparing said model transfer function with said actual transfer function.

51. The method of claim 34 further comprising, determining said characteristic of said pipeline at least in part by comparing an actual reflected component with a model reflected component.

52. The method of claim 37, wherein said input waveform comprises a plurality of input signals within said range of frequencies.

53. The method of claim 37 further comprising, detecting differences in velocity between said plurality of input signals as said input signals propagate in said pipeline, and determining a curvature of said pipe along said longitudinal axis from said differences in velocity.

54. The method of claim 52 further comprising, detecting differences in velocity between reflected components of each of said plurality of input signals to determine a curvature of said pipeline along said longitudinal axis.

55. A method of determining a location of a point along a pipeline, said method comprising,
  transmitting an input waveform having a selected input energy along a longitudinal axis inside said pipeline,
  receiving a reflected component of said input waveform from said pipeline, said reflected component having a characteristic reflected energy, and
  comparing said input waveform with said reflected component of said input waveform to determine said location of said point along said pipeline,
    wherein the transmitting, receiving, and comparing steps occur in a fashion that is non-invasive to the pipeline.

56. A method of inspecting a characteristic of a pipeline, said method comprising,
  generating an input waveform,
  launching said input waveform along a longitudinal axis inside said pipeline,
  receiving from said pipeline a reflected component having a characteristic reflected energy of said input waveform,
  calculating a mathematical function of said characteristic reflected energy from said reflected component of said input waveform,
  determining a model mathematical function of model reflected energy from a model component of a model input waveform, and
  determining said characteristic of said pipeline by comparing said mathematical function of said reflected energy to said model mathematical function of said model reflected energy,
    wherein each step is performed in a fashion that is non-invasive to the pipeline.

* * * * *